United States Patent [19]

Meltzer

[11] Patent Number: 5,055,263
[45] Date of Patent: Oct. 8, 1991

[54] AUTOMATED PIPETTING SYSTEM

[75] Inventor: Walter Meltzer, New Milford, Conn.

[73] Assignee: Cyberlab, Inc., Stamford, Conn.

[21] Appl. No.: 144,576

[22] Filed: Jan. 14, 1988

[51] Int. Cl.⁵ .......................... G01N 3/02; B01L 1/14
[52] U.S. Cl. .................. 422/65; 73/864.24; 73/864.25; 422/63; 422/81; 422/99; 422/100; 422/104; 436/180; 436/809
[58] Field of Search ............... 422/100, 99, 104, 81, 422/63, 67, 68, 65; 436/180, 809; 73/864.25, 864.14, 864.17, 863.32, 864.24

[56] References Cited

U.S. PATENT DOCUMENTS

| | | | |
|---|---|---|---|
| 3,687,632 | 8/1972 | Natelson | 422/100 X |
| 4,223,558 | 9/1980 | Schmider et al. | 422/100 X |
| 4,327,595 | 4/1982 | Schultz | 73/864.17 X |
| 4,341,736 | 7/1982 | Drbal et al. | 422/100 |
| 4,351,799 | 9/1982 | Gross et al. | 422/67 X |
| 4,452,899 | 6/1984 | Alston | 422/100 X |
| 4,456,037 | 6/1984 | Gocho | 422/100 X |
| 4,459,864 | 7/1984 | Cirincione | 422/100 X |
| 4,478,094 | 10/1984 | Salomaa et al. | 422/65 X |
| 4,586,546 | 5/1986 | Mezei et al. | 422/100 X |
| 4,593,837 | 6/1986 | Jakubowicz et al. | 73/864.17 X |
| 4,632,808 | 12/1986 | Yamamoto et al. | 422/67 X |
| 4,679,446 | 7/1987 | Sheehan et al. | 422/100 X |
| 4,734,261 | 3/1988 | Koizumi et al. | 422/100 |
| 4,757,437 | 7/1988 | Nishimura | 422/100 X |
| 4,785,677 | 11/1988 | Higo et al. | 422/100 X |
| 4,803,050 | 2/1989 | Mack | 422/67 X |

Primary Examiner—Robert J. Warden
Assistant Examiner—Amalia L. Santiago
Attorney, Agent, or Firm—Klein & Vibber

[57] ABSTRACT

An automated pipetting system for performing programmed pipetting procedures on an array of fluid containing test tubes, vials or wells. The system includes a frame which is placed above a horizontal table which holds the array. The frame is equipped with a pair of X-axis guide shafts and a pair of X-axis helical screw shafts. A subframe which is mounted on the X-axis guide shafts is equipped with a pair of Y-axis guide shafts and a Y-axis helical screw shaft. A carriage is mounted on the Y-axis guide shafts and at least one row of probes is mounted on the carriage. A Z-axis drive independently drives the probes in a Z-axis direction relative to the array.

8 Claims, 5 Drawing Sheets

AUTOMATED PIPETTING SYSTEM

BACKGROUND OF INVENTION

This invention relates to an automated pipetting system and, particularly, to a system with multiple pipetting probes which have individual positioning and individual metering controls.

Conventional automated pipetting systems are used to perform repetitive laboratory mixing, sampling or transferring of fluids in multiwell plates or multiple sets of vials or test tubes. Generally, one or more probes having fluid carrying tips are manipulated over an array of tubes by an arm which is robotically driven in three dimensions (X, Y, Z axes) to carry out programmed procedures under control of an associated computer. Desired procedures include dropping measured quantities of fluid from the tips into the tubes, taking fluid samples from the tubes into the tips, delivering measured quantities into fluids in the tubes at specified depths, prewetting the probes' tips, blowing out the tips to clear them, touching the tips to samples or a cleaning surface and changing the tips.

However, conventional pipetting systems have a number of limitations. Many systems have only one probe with one tip. Some systems have changeable pipette heads with multiple tips in parallel, but all tips are controlled together so that each one dispenses the same amount as the others. A few systems have independently dispensing probes, but they are not independently driven in the Z-axis (vertical) direction because the space taken up by the probe drive mechanisms would not fit the desired tight spacing of the plate wells or test tube array. Therefore, such systems can only drive all the probe tips together to the same depth in the wells or tubes. The smallest quantity which conventional probes can accurately dispense is usually of the order of 10 microliters. Since the probe or probes are usually mounted on a carriage movable along a cantilevered arm, these systems have the problem that the tips cannot be positioned with a high degree of precision due to mechanical bending or bowing or to misalignment.

SUMMARY OF INVENTION

It is, therefore, a prinicpal object of the invention to provide an automated pipetting system having a plurality of independently driven and independently dispensing probes which fit the tight spacing for multiwell plates and test tube arrays. It is intended that each probe can be positioned, particularly in the Z-axis direction, with a high degree of precision and controlled to handle a quantity of fluid as small as one microliter accurately. A further object of the invention is to provide a carriage moving mechanism which is very stable, operates smoothly and accurately, and maintains a precise structural alignment.

In accordance with the above purposes, the automated pipetting system of the invention has a rigid overhead frame above a table for the test tube or multiwell arrays, a pair of X-axis guide shafts spaced apart in parallel on two opposite sides of the frame, a pair of X-axis helical screw shafts each disposed in parallel with a respective X-axis guide shaft, a subframe driven in the X-axis direction by the X-axis screw shafts and having its opposite ends rolling on the X-axis guide shafts, a pair of Y-axis guide shafts supported on the subframe in parallel with each other, a Y-axis helical screw shaft in between the two Y-axis guide shafts, a carriage driven in the Y-axis direction by the Y-axis screw shaft and rolling on the Y-axis guide shafts, and at least one row of probes having separate drive mechanisms for independent Z-axis (vertical) movement on the carriage, wherein the drive mechanisms are stacked vertically one above another on each side of the row of probes and each mechanism controls a respective probe by an output shaft of a given length extending from the drive mechanism to the row position of the respective probe.

In the above construction, the frame, X and Y-axis screw shafts and guide shafts allow precise positioning of the carriage in the X and Y directions. The subframe and the carriage each have translation rollers rolling on the top surfaces of the corresponding guide shafts and spring-biased positioning rollers oriented perpendicular to the translation rollers for keeping the moving part in precise alignment with the guide shafts. The stacked arrangement of the probe drive mechanisms allows four or more probes to be positioned close together in a row according to the tight spacing of the multiwell or test tube array. Two or more such rows of indpendently driven probes may be used.

In the preferred embodiment of the invention, eight probes are arranged in two rows of four each. The probes are fixed on the ends of linear racks each of which is independently driven by a pinion gear on the output shaft of the respective drive mechansim. Three of the four probes in each row are connected to external syringe pumps via tubing that passes through a hole bored in the Z-axis racks and exits from the side of casing 17. Similarly, the other probes in each row are connected to one channel each of the peristaltic pump. The syringe pumps draw small to moderate quantities of fluid (1-5000 ul) into the disposable pipette tips. The peristaltic pump draws larger quantities of fluid (up to 2 liters/hours) continuously through the two nondisposable probe tips and connecting tubing. The syringe pumps are external units consisting of three syringes each and a choice of two sizes (1 ml and 5 ml). The syringes have a nylon body with a fixed tensioned teflon seal inset into the top of the cylinder and a centerless ground stainless steel piston shaft. The peristaltic pump, also an external unit, is a two channel, 15 roller design with rigidly adjusted shoes and stepper motor driven. The syringes are also stepper motor driven via fine pitched rack and pinions. Different combinations or pumps of another manufacture may also be used since all eight probes are identical in construction. Interchangeable tip holders are screwed onto the bottom of the Z-axis racks and can pickup or discharge disposable pipette tips via downward or upward motion of the linear racks.

The peristalitc pump is also external and any numerical combination of peristaltic and syringe pumps or pumps of another manufacture may be used. The probes have interchangeable tip holders which can pick up or discharge different size disposable pipettte tips.

The helical screw shafts of the X-Y positioning frame are driven by stepper motors and microswitches are provided to mark the home position of the carriage. After a tip change, the probes are recalibrated for the Z-axis positions of the tips by moving the probe tip to a maximum downward position, which also seats the new tip on the tip holder, and then moving the probe tip back upward to a home position detected by a microswitch while an associated computer counts the number of steps. The computer, thereafter, tracks the Z-axis position of the tip by storing and updating the step count in memory, so that the tip can be stepped accurately to a specified depth in a test tube.

BRIEF DESCRIPTION OF DRAWINGS

The above objects, features and advantages of the invention are described in greater detail below, in conjunction with the drawings, of which.

DETAILED DESCRIPTION OF INVENTION

Figure 1:
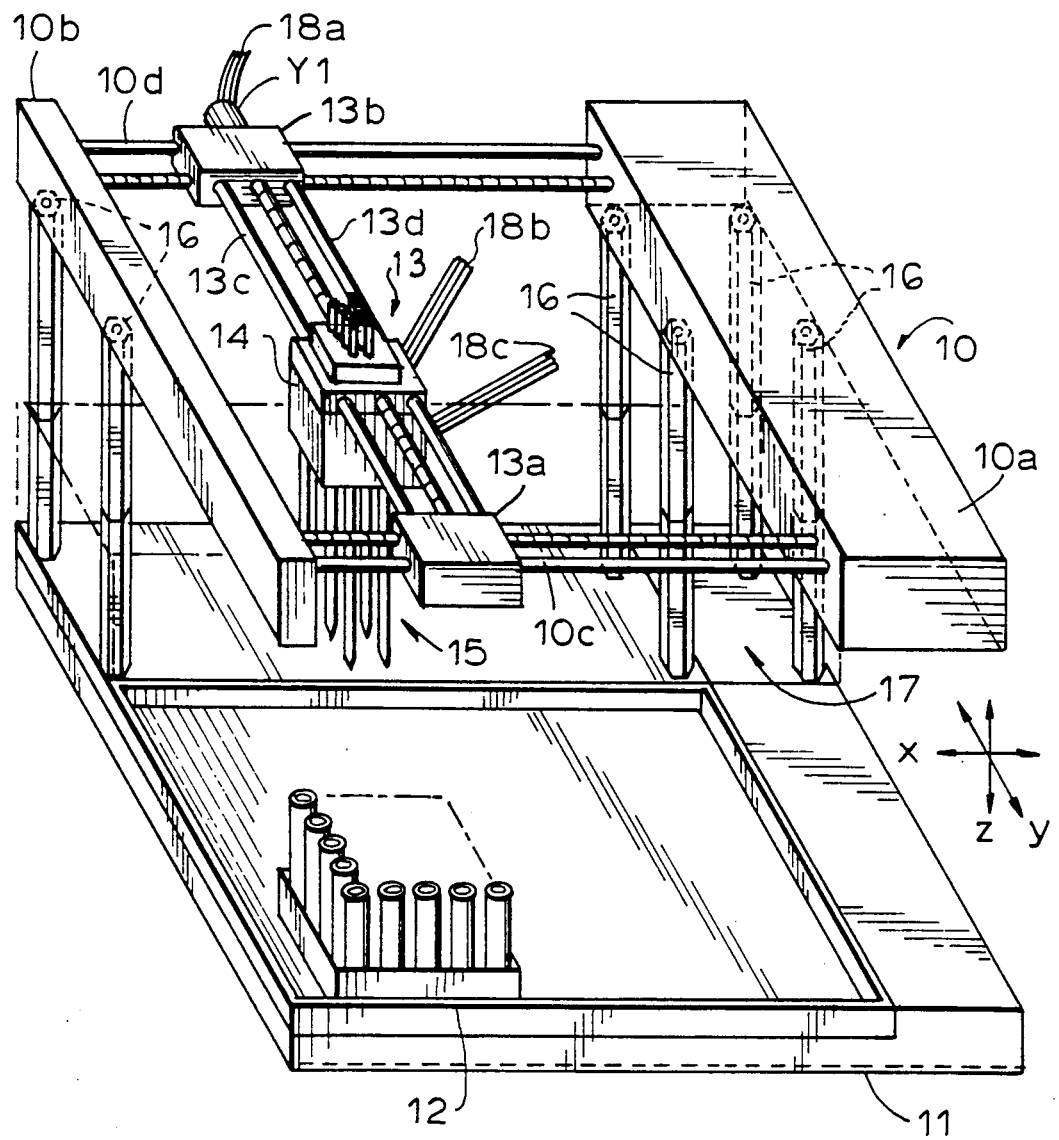
FIG. 1 is a perspective view of an automated pipetting system in accordance with the invention.
Figure 2:
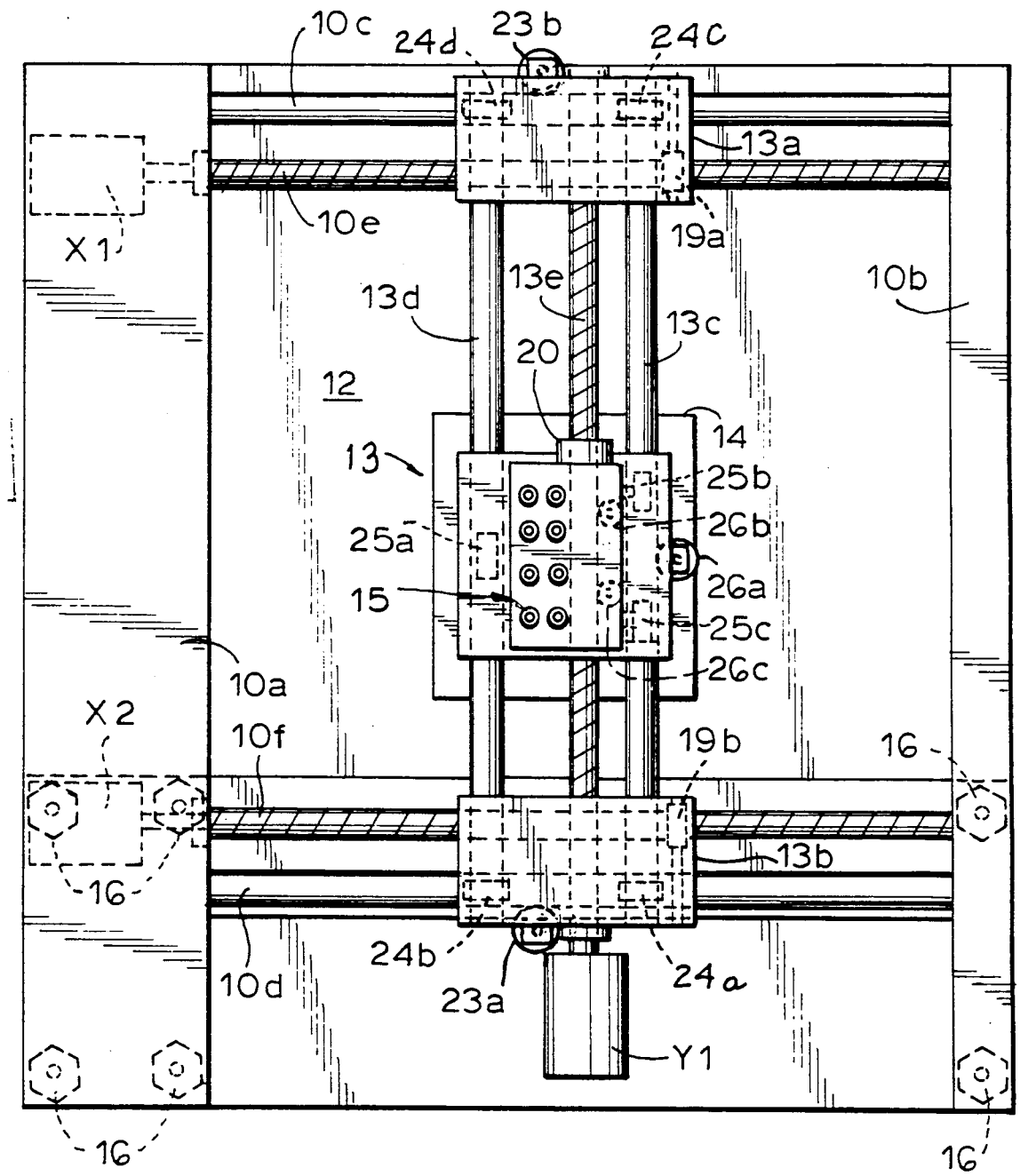
FIG. 2 is a schematic plan view of a three dimensional (XYZ axes) moving mechanism for a carriage of the system of FIG. 1.

Referring to FIGS. 1 and 2, an automated pipetting system, in accordance with the invention, has an overhead frame assembly indicated generally by reference numeral 10 having frame sides 10a and 10b, subframe assembly 13 supported on roller sections 13a and 13b on guide shafts 10c and 10d of frame 10 for movement in the X-axis directions and carriage 14 supported on guide shafts 13c and 13d of subframe assembly 13 for movement in the Y-axis directions. Base 11 supports table 12 for holding multiwell plates or test tubes arrays on which the pipetting procedures are performed. Water bath tray 12 sits on top of base 11, so that the test tube arrays are located within the X-Y range of movement under carriage 14. The tray has locater pins to locate the test tubes, microwells, beakers, etc., in particular, subsections of the table surface.

Carriage 14 carries a number of probes 15 which, in this described embodiment, are shown arranged in two rows of four probes each. Probes 15 are independently movable in the Z-axis directions by separate, stacked drive units, to be described further below. Overhead frame assembly 10 is supported rigidly above table 12 by vertical supports 16. Chassis 17 houses the electronics and power supply for driving the subframe, carriage, and probe moving mechanisms shown schematically connected thereto by cables 18a, 18b, and 18c.

As shown in FIG. 2, frame assembly 10 includes two helical screw shafts 10e and 10f, each disposed adjacent and in parallel with one of guide shafts 10c and 10d, respectively. Two stepper motors drive X1 and X2 and are housed within frame side 10a for rotating screw shafts 10e and 10f. Subframe roller sections 13a and 13b have helix nuts 19a and 19b engaged with the threads of X-axis screw shafts 10e and 10f for driving the roller sections in the X-axis directions in accordance with rotation of the shafts by stepper motor drives X1 and X2.

Subframe assembly 13 has one helical screw shaft 13e disposed between Y-axis guide shafts 13c and 13d. Stepper motor drive Y1 is mounted through the rear side of roller section 13b for rotating screw shaft 13e. Carriage 14 has helix nut 20 engaged with the threads of Y-axis screw shafts 13e for driving the carriage in the Y-axis directions upon rotation of the shaft by stepper motor drive Y1.

Figure 3:
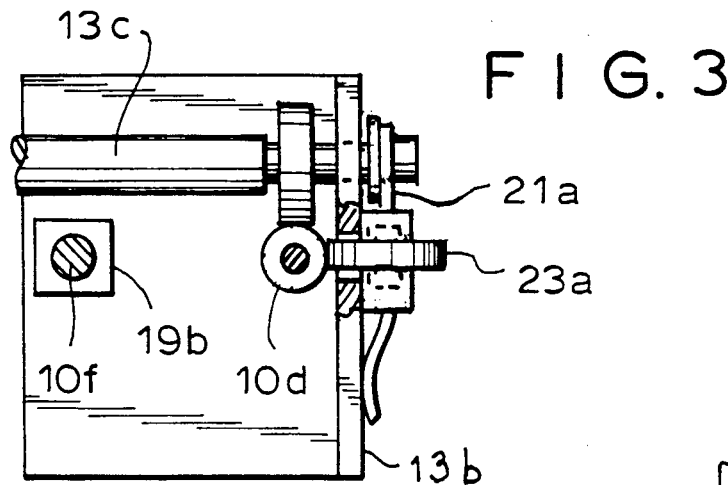
FIG. 3 is a side schematic view of one roller section of the X-axis moving mechanism for the system of FIG. 1.
Figure 4:
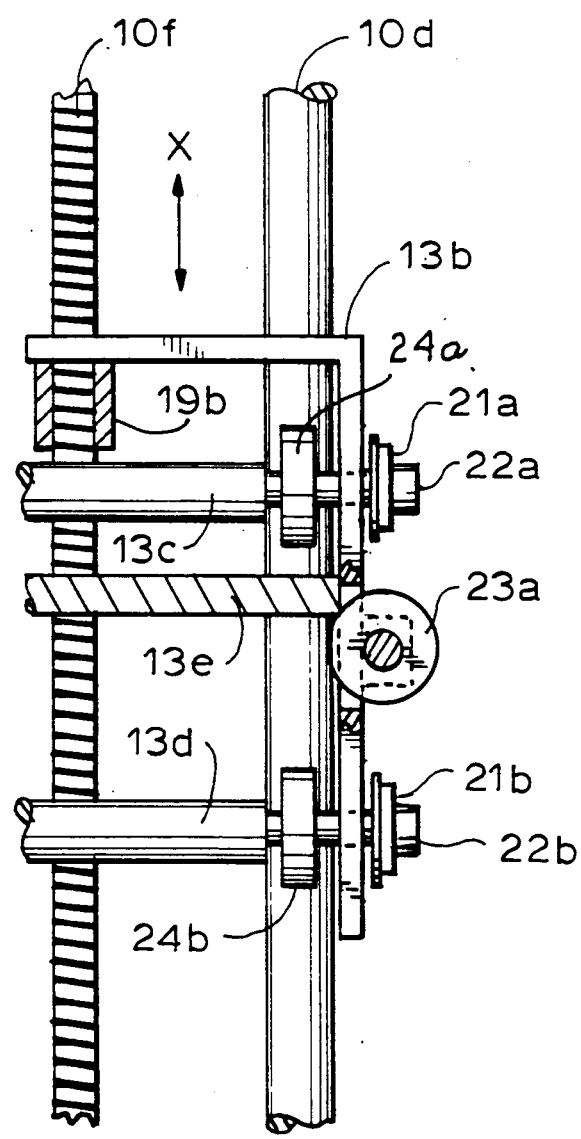
FIG. 4 is a plan schematic view of the roller section of the X-axis moving mechanism.

The construction of roller sections 13a and 13b rolling on guide shafts 10c and 10d, is shown in greater detail in FIGS. 3 and 4 in side and plan view, respectively. Both roller sections are similarly constructed, so only one section is described herein. The rear wall of roller section 13b supports the ends of Y-axis guide shafts 13c and 13d and screw shaft 13e. The ends of guide shafts 13c and 13d are tensioned by flat springs 21a and 21b, which are pressed between the side roller section 13b and end caps 22a and 22b. Translation roller 24a and 24b are freely rotatable on the ends of shafts 13c and 13d as they roll on guide shaft 10d when screw shaft 10f is rotated to move roller section 13b by means of helix nut 19b. They are maintained in position on the guide shaft 10d by positioning roller 23a which is oriented perpendicular to translation rollers 24a and 24b and presses against the side of guide shaft 10 under the tensioning force exerted by flat springs 24a and 21b.

Figure 5:
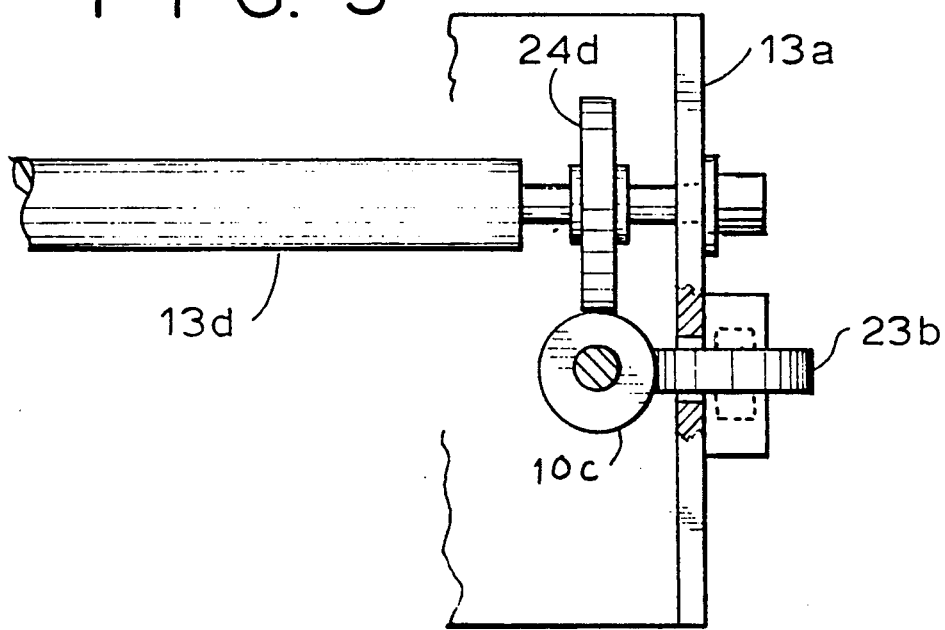
FIG. 5 is a side schematic view of the other roller section of the X-axis moving mechanism for the system of FIG. 1.
Figure 6:
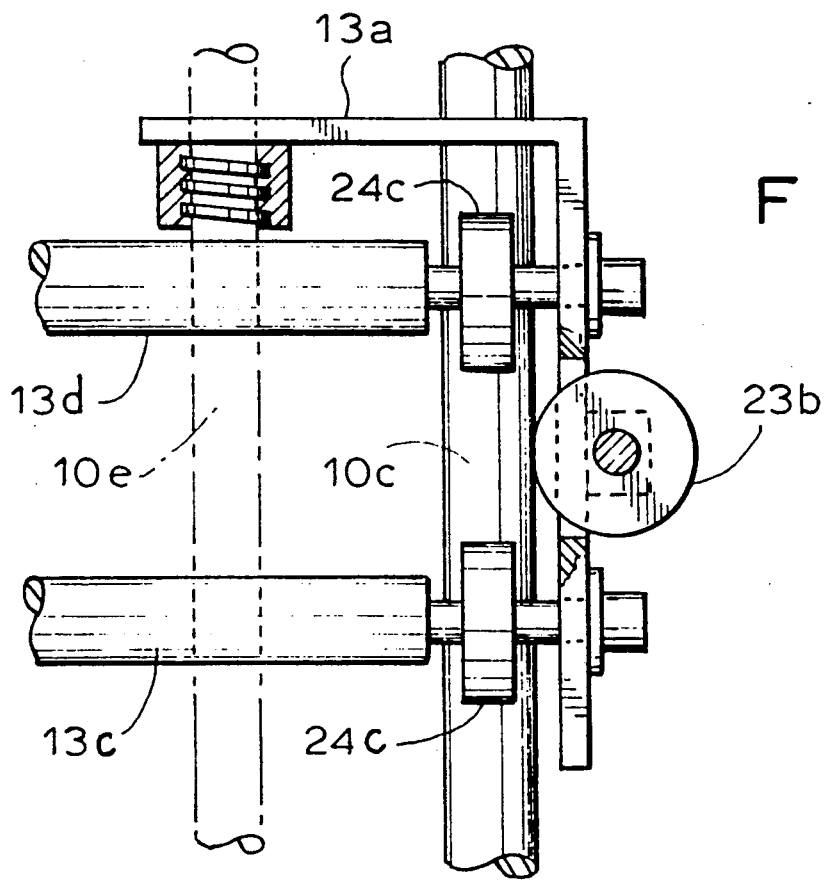
FIG. 6 is a plan schematic view of the other roller section of the X-axis moving mechanism.

Referring to FIGS. 5 and 6, the other ends of guide shafts 13c and 13d are fixed in the front wall of roller section 13a and need not be spring-tensioned. Similarly, roller section 13a has translation rollers 24c and 24d and positioning roller 23b, which is pressed against the side of guide shaft 10c by flat spring 21c and by the tension force of flat springs 21a and 21b applied at the other roller section 13b, as described above. Roller sections 13a and 13b may also be provided with spring-biased translation rollers on the lower sides of the guide shafts, and positioning rollers on the opposite sides of the guide shafts 10c and 10d from positioning rollers 23a and 23b for a more positive clamping effect on guide shafts 10c and 10d.

The shafts are not torsionally fixed to 13b allowing all four rollers to seat. Carriage 14 has translation rollers 25a, 25b and 25c rolling on Y-axis guide shafts, roller 25d located underneath 13c for clamping action and positioning rollers 26a, 26b and 26c clamped in rolling contact on opposite sides of guide shaft 13c in a plane perpendicular to the rolling plane of the translation rollers.

The helical screw shafts of the X-Y positioning frame and subframe assemblies are driven by the stepper motors to target positions specified by an associated computer controlling the programmed procedures for the pipetting system. A computer communication link is provided by connectors to casing 17 to the electronic controls for the pipetting drive and dispensing mechanisms. The frame and subassembly positioning controls are calibrated by microswitches provided to mark the home position of the carriage in the X-Y plane. Other home position detectors may, of course, be used, such as optical or magnetic detectors.

Figure 7:
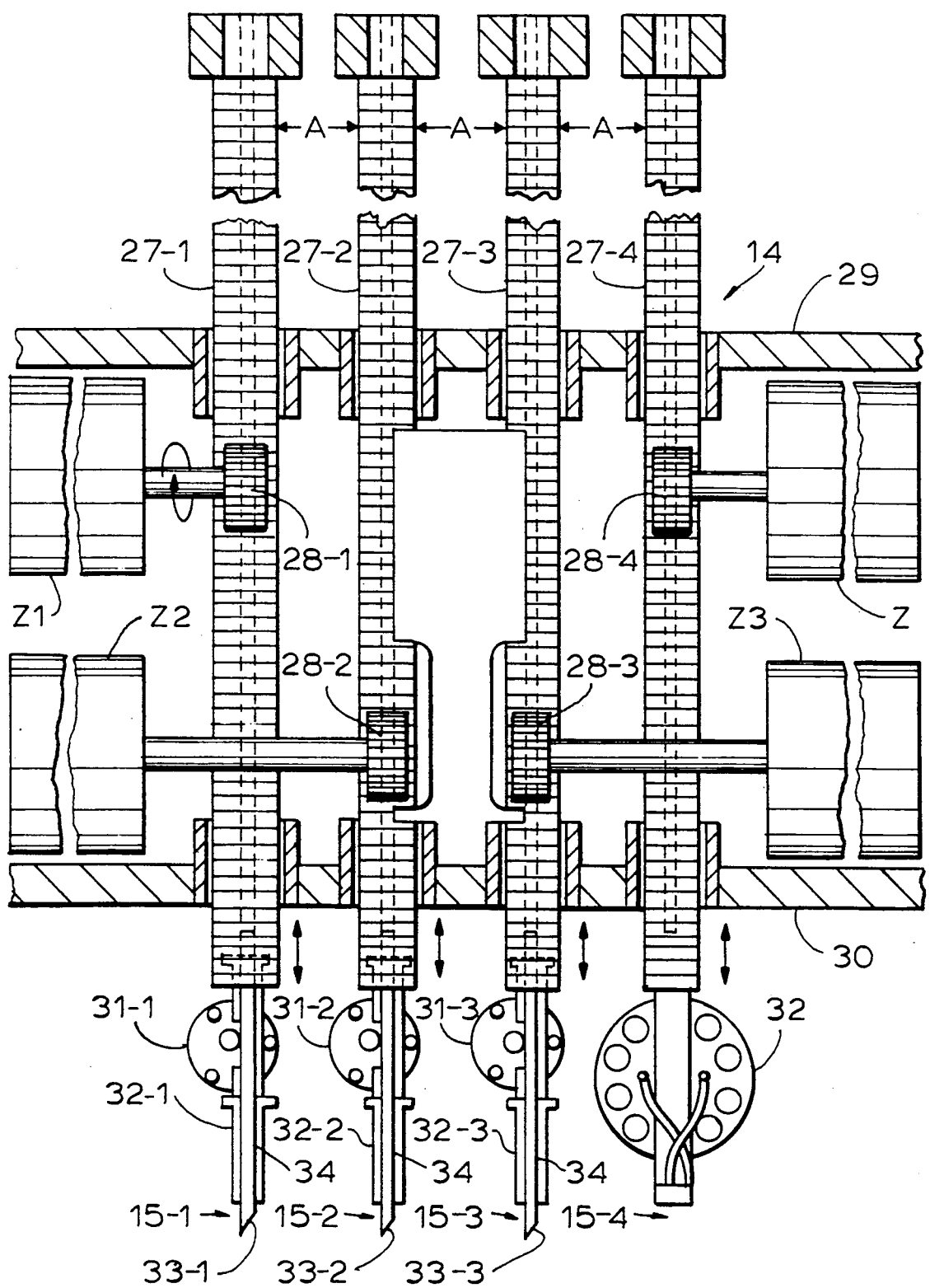
FIG. 7 is a side sectional view of a probe Z-axis driving mechanism for the system of FIG. 1.

Referring to FIG. 7, carriage 14 houses the driving mechanisms for the probes in the form of linear racks 27-1, 27-2, 27-3 and 27-4 shown for one row of probes. Stepper motors Z1, Z2, Z3 and Z4 drive the linear racks in the Z-axis directions by means of pinion gear 28-1, 28-2, 28-3 and 28-4 fixed to the output shafts of the respective motors. The motors are arranged in stacked configuration, one above the other, on each side of the row of racks, so as to allow the racks, and therefore the probes, to be spaced close together with spacing A corresponding to the standard configuration for test tube arrays, typically ¾ inch on centers. The linear racks 27-1, 27-2, 27-3 and 27-4 are slidable in bushings provided through upper and lower walls 29 and 30 of carriage 14. The carriage is shown holding two rows with four probes in each row, however, additional probes in each row or additional rows may be provided.

The probes 15-1, 15-2, 15-3 and 15-4 are fixed to the lower ends of linear racks 27-1, 27-2, 27-3 and 27-4. In the preferred configuration, external syringe pumps 31-1, 31-2, 31-3 are provided for three of the probes for pipetting functions (housed in one external unit), and an external peristaltic pump 31-4 is provided for the fourth probe for bulk dispensing or transferring of fluid. The syringe pumps have narrow cylinders (for accuracy) and thin, centerless ground, stainless steel piston shafts output to tubes 32, and which are driven by fine-pitched rack and pinion drives (for greater pipetting control). Spring-biased teflon sleeves are provided on the piston shaft held by O-rings to provide an air-tight seal for suction or pressure against fluid being manipulated by the syringe pumps. The large ratios of the piston shaft lengths to their dimensions allow the fluid metering to be highly accurate. The syringe pumps only draw fluid into the pipette tips. Fluid never enters the syringe. The 15 roller peristaltic pump allows continuous, low pulsation flow for large fluid volumes and for pumping end product samples to an output device such as a spectrophoto.

Figure 8:
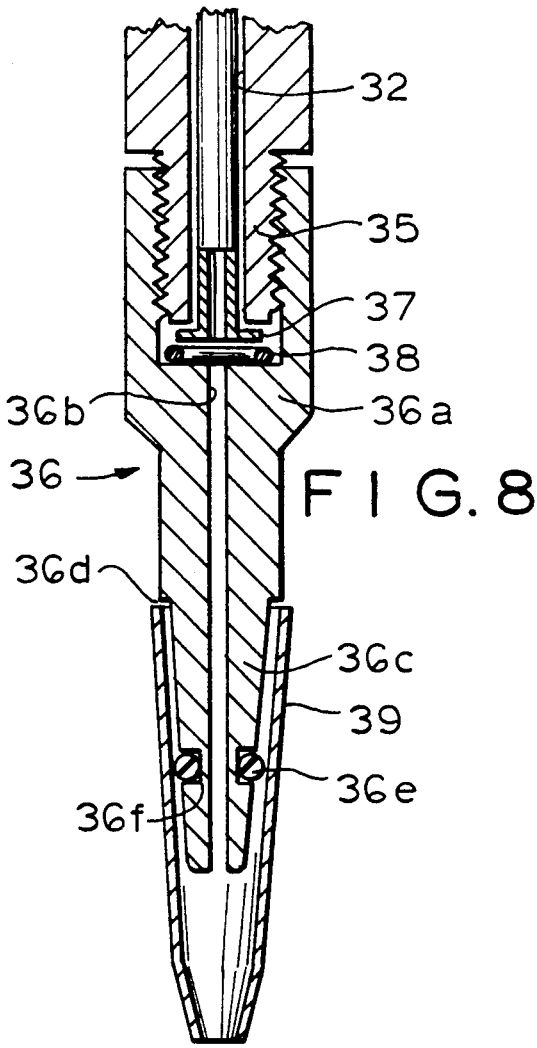
FIG. 8 is a side sectional view of a tip holder with a changeable tip for the probe.

The lower ends of the Z-axis racks are threaded for screwing into tip holders, as shown in more detail in FIG. 8. Threaded end 35 is screwed into receptable end 36a of tip holder 36, clamping a nylon top hat 37 and O-ring 38 at its lower portion as a fluid seal. Passage 36b of tip holder 36 communicated into tubing 32 which is pressed over top hat 37 and passes through hollow rack 27 into casing 17 exiting on side for connection to external pumps. Lower end of tip holder 36 has a slight taper for smoothly inserting into the similarly tapered end of disposable tip 39. Shoulder 36c is provided for abutting against the upper end of tip 39, so that it is positively positioned and held on tip holder 36. O-ring 36e held in groove 36f formed on tip holder 36 provides an air-tight seal and a friction surface for retaining tip 39 on the tip holder.

Tips for the probes may be selected from a range of sizes, such as from 200 to 5000 microliters. The use of the syringe pumps allow fluid quantities as small as 10 microliters to be dispensed with one percent accuracy and quantities of one microliter with two percent accuracy, when the tip ends are touched on or dipped below the surface of the fluid in the test tubes to break the surface tension. Tips 39 are attached on or removed from tip holders 36 by X-Y movement of carriage 14 to the location of the fresh tips on table 12, then by downward Z movement of the probes, driven linear racks 27 and the Z-axis motors, until the shoulders 36d of the tip holders are seated against the upper ends of the tips and ending with a return movement of the probes. Removal is accomplished by a converse movement to maneuver the upper shoulder of the tip under a V shaped shoe and a detaching upward movement of the probes. Up to four pipette tips, in a single row, can be removed simultaneously. At the latter part of a tip change, the probes are recalibrated for the Z-axis positions of the tips by moving the probe tip holders to a maximum downward position, which also seats the new tips on the tip holders, and then moving the probe tips back upward to home positions detected by microswitches or other forms of position detectors. The associated computer counts the number of steps between the maximum downward positions and the home positions and stores the information. The computer, thereafter, tracks the Z-axis position of the tips by updating the step count in memory, so that the tip can be stepped accurately to the specified target depths in the test tube arrays. The system in practice provides a working accuracy to within 0.005 inch over six inches of probe travel.

Other features of the automated pipetting apparatus can include an elliptical pattern shaker unit coupled to the underside of table 12 for mixing the samples in the arrays held on the table. Also, a water bath and temperature controls can be used to provide water into a holding tray or trays on table 12 at the temperatures required to maintain the test tube samples thereon at a desired temperature. The trays or table may have different temperature sections. The apparatus may also have a display panel to provide visual confirmation of the status of the programmed procedures being executed by the apparatus. Computer programs for automatically controlling the operation of the pipetting apparatus are used conventionally and are not described herein.

In accordance with the invention, the provision of a frame assembly framing the boundaries of the X-Y pipetting area and the subframe assembly rolling by roller sections on the guide shafts disposed at opposite sides of the frame allow the X-Y positioning of the carriage to be carried out accurately and stably with a minimum of misalignment due to bending, bowing or mechanical deflection. The spring-tensioning of the guide shafts of the subframe assembly foregoes the necessity of the two guide shafts having to be parallel to a high degree of precision. The Z-axis motors are arranged in stacked configuration to allow a close spacing of the probes to fit the spacings of the test tube arrays. The high precision syringe pumps coupled with the capability of putting the pipette tips accurately and reliably just below the surface of the liquid provide the capability to dispense minute quantities of fluid with high accuracy. The use of microswitches and XYZ home position calibration ensure precise positioning of the tips relative to the test tube arrays and their fluid levels. All of these features and advantages achieve a greatly improved functioning of the automated pipetting system over conventional apparatus.

Although a preferred embodiment of the invention has been described above, it should be understood that many variations and modifications are possible within the disclosed principles of this invention. For example, the placement of the guide shafts and screw shafts may be varied, other forms of XYZ drives may be used, and the configuration of the various roller sections may be modified. It is intended that the embodiment described herein and all such variations and modifications be included within the scope of the invention, as defined in the following claims.

I claim:

1. An automated pipetting system for performing programmed pipetting procedures on an array of fluid containing test tubes, vials, or wells, comprising:
   a rigid overhead frame defining a horizontal X-Y pipetting area, which is supported and spaced vertically above a horizontal table for holding test tube arrays;

a pair of X-axis guide shafts fixedly mounted and spaced apart in parallel on two opposite sides of the frame;

a pair of X-axis helical screw shafts rotatably mounted in the frame, each disposed adjacent and parallel to a respective one of said X-axis guide shafts, and X-axis drive means for driving said screw shafts synchronously in rotation;

a subframe having roller sections extending at opposite ends thereof rolling on the X-axis guide shafts, said roller sections each having a support wall provided with a helix engagement portion engaging said X-axis helical screw shafts for moving said subframe in the X-axis directions in response to rotation thereof;

a pair of Y-axis guide shafts supported on the subframe spaced apart parallel to each other;

a Y-axis helical screw shaft rotatably mounted in the subframe between and parallel to the two Y-axis guide shafts, and Y-axis means for driving said screw shaft in rotation;

a carriage having a pair of roller sections rolling on the Y-axis guide shafts, and a support wall provided with a helix engagement portion engaging said Y-axis helical screw shaft for moving said carriage in the Y-axis directions in response to rotation thereof; and at least one row of probes mounted on said carriage for movement in the Z-axis directions, and Z-axis drive means for independently driving respective ones of said probes in the Z-axis directions relative to the test tube array on said table wherein said X, Y and Z axes respectively define mutually perpendicular planes.

2. An automated pipetting system according to claim 1, wherein ends of said Y-axis guide shafts are resiliently mounted in one roller section by means of plate springs provided between a support wall of said roller section and a retaining portion secured to the ends of the Y-axis guide shafts.

3. An automated pipetting system for performing programmed pipetting procedures on an array of fluid containing test tubes, vials, or wells, comprising:

a rigid overhead frame defining a horizontal X-Y pipetting area, which is supported and spaced vertically above a horizontal table for holding the test tube arrays;

a pair of X-axis guide shafts fixedly mounted and spaced apart in parallel on two opposite sides of the frame;

a subframe having roller sections at opposite ends thereof rolling on the X-axis guide shafts.

X-axis moving means connected to for moving the subframe in the X-axis directions on the X-axis guide shafts of the frame;

a pair of Y-axis guide shaft supported on the subframe spaced apart parallel to each other;

a carriage having a pair of roller sections rolling on the Y-axis guide shafts;

Y-axis moving means connected to for moving the carriage in the Y-axis directions on the Y-axis guide shafts of the subframe; and at least one row of probes mounted on said carriage for movement in the Z-axis directions, and Z-axis drive means for independently driving respective ones of said probes in the Z-axis directions relative to the test tube array on said table;

wherein said Z-axis drive means include linear racks mounted to the upper ends of the probes, and separate drive units for driving the linear racks of the respective probes which drive units are stacked vertically one above another on each side of the at least one row of probes and said drive units are parallel with the linear racks, each drive unit having an output shaft of a given length provided with a pinion gear its end extending from the drive unit to the row position of and engaged with a linerar rack for a respective one of the probes wherein said X, Y AND Z axes respectively define mutually perpendicular planes.

4. An automated pipetting system according to claim 3, wherein said Z-axis drive means has four stacked drive units, one above another on each side of the at least one row of probes.

5. An automated pipetting system according to claim 3, wherein the probes have respective syringe pumps for individually controlling the pipetting function of each probe.

6. An automated pipetting system according to claim 3, further comprising electronic control means for controlling the Z-axis driving of the probes, including means for calibrating the Z-axis positions of the probes.

7. An automated pipetting system according to claim 6, wherein the Z-axis drive units are stepper motors, and the calibrating means includes an associated computer connected to the electronic control means for storing and updating a step count for each probe in memory, so that each probe can be stepped accurately to a specified depth in a test tube.

8. An automated pipetting system according to claim 3, wherein said probes have tip holders on their respective lower ends for holding changeable tips thereon.

* * * * *